United States Patent
Curtis (10) Patent No.: US 9,259,528 B2
(45) Date of Patent: Feb. 16, 2016

(54) FLUID INFUSION DEVICE WITH SAFETY COUPLING

(71) Applicant: MEDTRONIC MINIMED, INC., Northridge, CA (US)

(72) Inventor: Mark S. Curtis, Castaic, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 13/973,877

(22) Filed: Aug. 22, 2013

(65) Prior Publication Data

US 2015/0057614 A1   Feb. 26, 2015

(51) Int. Cl.
*A61M 5/14* (2006.01)

(52) U.S. Cl.
CPC .................................. *A61M 5/1413* (2013.01)

(58) Field of Classification Search
CPC ..... A61M 5/1413; A61M 39/00; A61M 1/00; A61M 37/00; A61M 5/14244; A61M 5/14566; A61M 5/16827; A61M 5/14232; A61M 5/14546
USPC .................. 604/151, 523, 533–535
See application file for complete search history.

(56) References Cited

U.S. PATENT DOCUMENTS

| | | | |
|---|---|---|---|
| 2,706,984 A * | 4/1955 | Lipari | 604/200 |
| 3,631,847 A | 1/1972 | Hobbs, II | |
| 4,212,738 A | 7/1980 | Henne | |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |

(Continued)

FOREIGN PATENT DOCUMENTS

DE   4329229   3/1995
EP   0319268   11/1988

(Continued)

OTHER PUBLICATIONS

PCT Search Report (PCT/US02/03299), Oct. 31, 2002, Medtronic Minimed, Inc.

(Continued)

*Primary Examiner* — Imani Hayman
(74) *Attorney, Agent, or Firm* — Ingrassia Fisher & Lorenz, P.C.

(57) ABSTRACT

A safety coupling for a fluid infusion device is provided. The device includes a first coupling device coupled to a drive system of the fluid infusion device, and a second coupling device coupled to a stopper of a fluid reservoir associated with the fluid infusion device. The first coupling device and the second coupling device cooperate to resist the movement of the stopper relative to the drive system.

6 Claims, 6 Drawing Sheets

(56) References Cited

U.S. PATENT DOCUMENTS

| | | |
|---|---|---|
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |

(56) References Cited

U.S. PATENT DOCUMENTS

| | | | |
|---|---|---|---|
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,621,893 B2 | 11/2009 | Moberg et al. | |
| 7,828,764 B2 | 11/2010 | Moberg et al. | |
| 7,905,868 B2 | 3/2011 | Moberg et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2008/0269687 A1 | 10/2008 | Chong et al. | |
| 2009/0081951 A1 | 3/2009 | Erdmann et al. | |
| 2009/0082635 A1 | 3/2009 | Baldus et al. | |
| 2009/0099524 A1* | 4/2009 | Kirchhofer et al. | 604/151 |
| 2009/0299290 A1 | 12/2009 | Moberg | |
| 2013/0331791 A1* | 12/2013 | Gross et al. | 604/151 |
| 2013/0338592 A1* | 12/2013 | Calasso | 604/151 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII]With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(MiniMed, 1996). The MiniMed 506. 7 pages. Retrieved on Sep. 16, 2003 from the World Wide Web: http://web.archive.org/web/19961111054527/www.minimed.com/files/506_pic.htm.

(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.

(MiniMed, 1996). FAQ: The Practical Things . . . pp. 1-4. Retrieved on Sep. 16, 2003 from the World Wide Web: http://web.archive.org/web/19961111054546/www.minimed.com./files/faq_pract.htm.

(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.

(MiniMed Technologies, 1994). MiniMed 506 Insulin Pump User's Guide.

(MiniMed Technologies, 1994). MiniMed™ Dosage Calculator Initial Meal Bolus Guidelines / MiniMed™ Dosage Calculator Initial Basal Rate Guidelines Percentage Method. 4 pages.

(MiniMed, 1996). MiniMed™ 507 Insulin Pump User's Guide.

(MiniMed, 1997). MiniMed™ 507 Insulin Pump User's Guide.

(56) References Cited

OTHER PUBLICATIONS (MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intravenous Arginine in Human Diabetes Mellitus With the Artificial Beta-Cell," Diabetes vol. 29, Sep. 1980, pp. 762-765.

Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

(56) References Cited

OTHER PUBLICATIONS

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

FLUID INFUSION DEVICE WITH SAFETY COUPLING

TECHNICAL FIELD

Embodiments of the subject matter described herein relate generally to fluid infusion devices for delivering a medication fluid to the body of a user. More particularly, embodiments of the subject matter relate to systems for a fluid infusion device having a safety coupling.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. In most instances, the dispensing of the fluid from the fluid reservoir is metered according to the needs of a patient.

Accordingly, it is desirable to provide systems for a safety coupling that ensures proper delivery of fluid to the patient. Furthermore, other desirable features and characteristics will become apparent from the subsequent detailed description and the appended claims, taken in conjunction with the accompanying drawings and the foregoing technical field and background.

BRIEF SUMMARY

According to various exemplary embodiments, a safety coupling for a fluid infusion device is provided. The device includes a first coupling device coupled to a drive system of the fluid infusion device, and a second coupling device coupled to a stopper of a fluid reservoir associated with the fluid infusion device. The first coupling device and the second coupling device cooperate to resist the movement of the stopper.

Also provided according to various embodiments is a fluid infusion device. The device comprises a drive system that includes a movable slide. The slide includes a first coupling device. The device also comprises a fluid reservoir that includes a stopper movable relative to the fluid reservoir by the slide to advance a fluid out of the fluid reservoir. The stopper includes a second coupling device that cooperates with the first coupling device to resist the movement of the stopper relative to the slide.

An insulin infusion device is also provided according to various embodiments. The insulin infusion device comprises a drive system that includes at least a motor, a drive screw and a slide. The motor is operable to drive the drive screw to translate the slide and the slide has a first coupling device. The insulin infusion device also comprises a fluid reservoir removably coupled to the insulin infusion device that includes a stopper movable relative to a barrel of the fluid reservoir by the slide to advance a fluid out of the fluid reservoir. The stopper includes a counterbore that receives a portion of the slide and a second coupling device positioned adjacent to the counterbore that cooperates with the first coupling device to resist the movement of the stopper relative to the slide. One of the first coupling device and the second coupling device include a permanent magnet and the other of the first coupling device and the second coupling device include a magnetically attractive material.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

Figure 1:
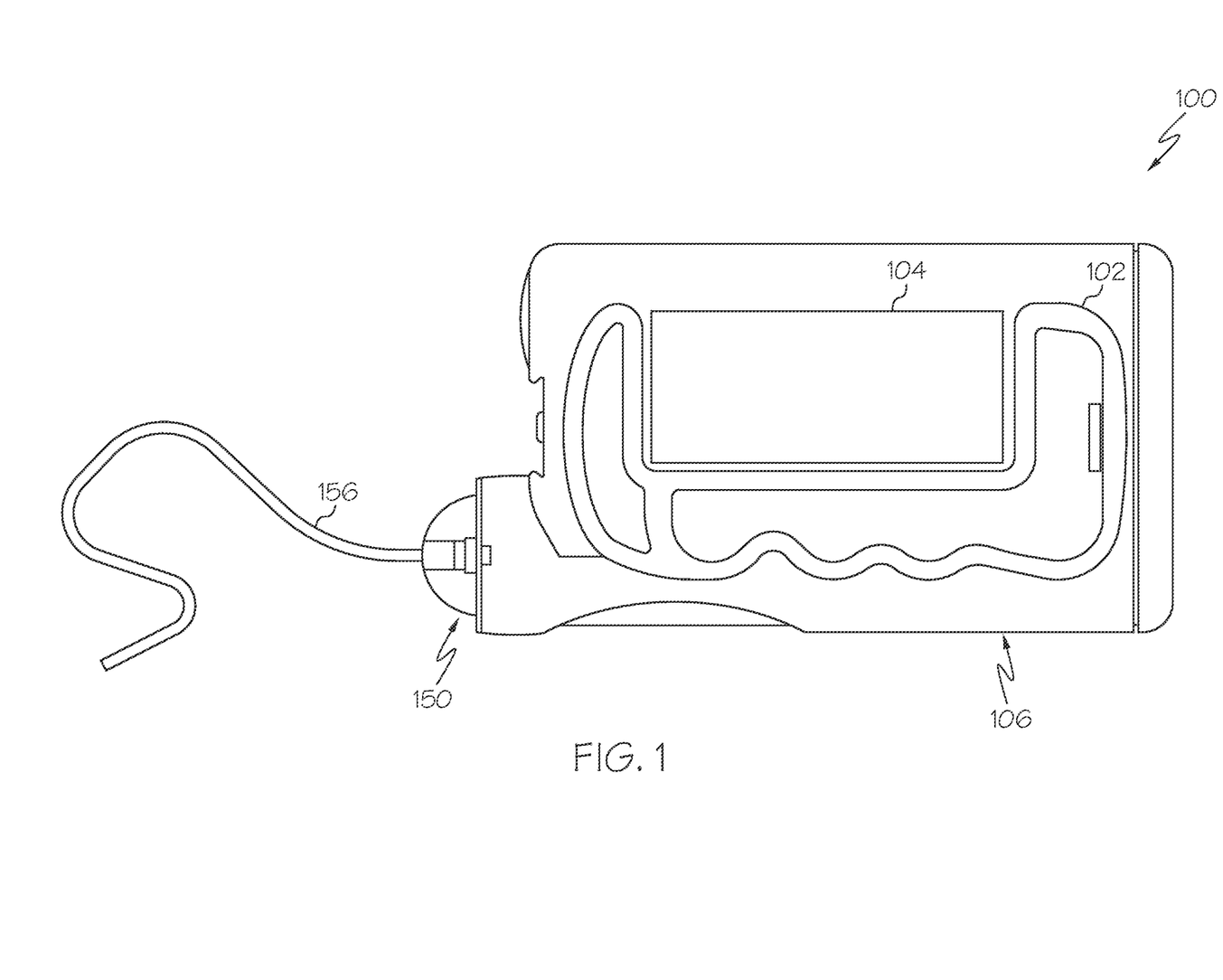
FIG. 1 is a perspective view of an exemplary embodiment of a fluid infusion device according to various teachings of the present disclosure.
Figure 1A:
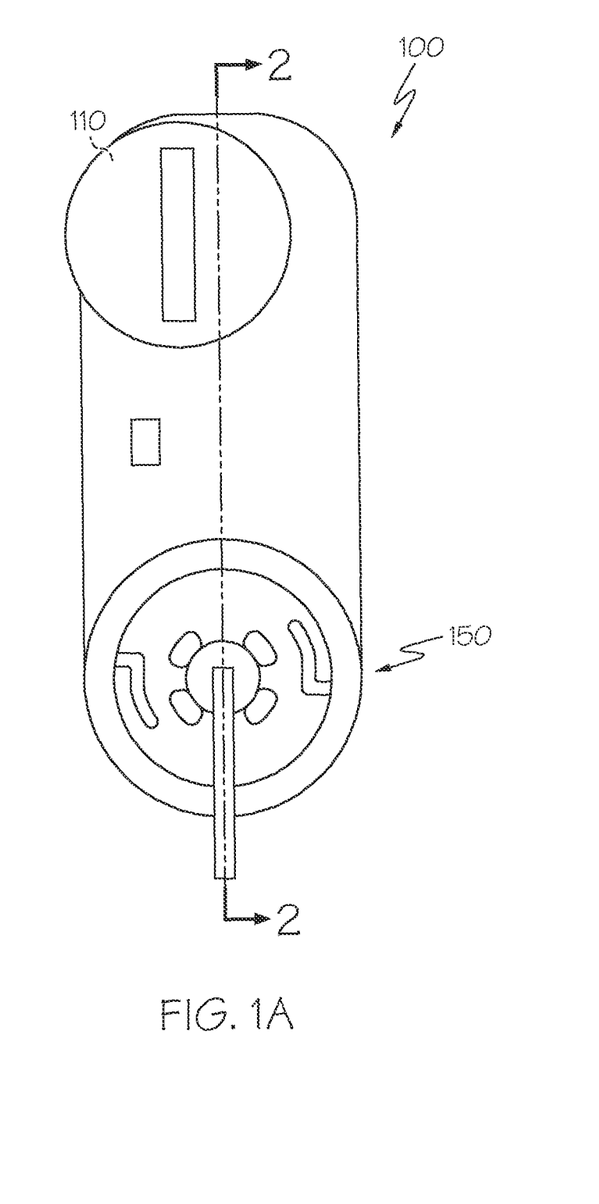
FIG. 1A is a top view of the fluid infusion device of FIG. 1.

FIG. 1 is a perspective view of an exemplary embodiment of a fluid infusion device 100, and FIG. 1A is a top view of the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

With reference to FIG. 1, the fluid infusion device 100 includes a user interface 102 and a display 104 coupled to a housing 106. The user interface 102 includes one or more user input devices, such as buttons, which can be activated by the user. The user interface 102 can be used to administer a bolus of insulin, to change therapy settings, to change user preferences, to select display features, and the like. Although not required, the illustrated embodiment of the fluid infusion device 100 includes the display 104. The display 104 can be used to present various types of information or data to the user, such as, without limitation: the current glucose level of the patient; the time; a graph or chart of the patient's glucose level versus time; device status indicators; etc. In some embodiments, the display 104 is realized as a touch screen display element and, therefore, the display 104 also serves as a user interface component.

Figure 2:
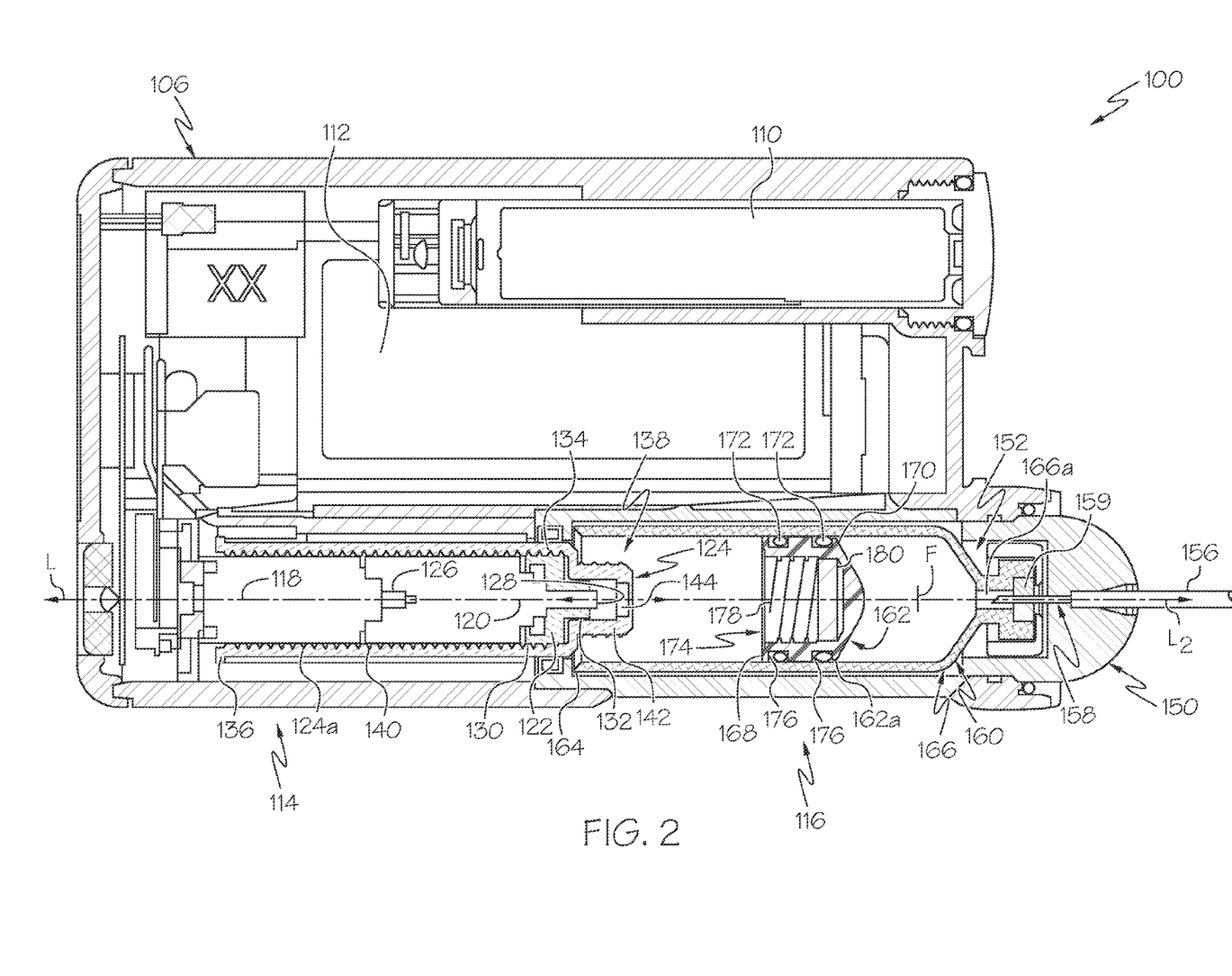
FIG. 2 is cross-sectional view of the fluid infusion device of FIG. 1, taken along line 2-2 of FIG. 1A.

With reference to FIG. 2, the housing 106 of the fluid infusion device 100 accommodates a power supply 110, a controller 112, a drive system 114 and a fluid reservoir system 116. The power supply 110 is any suitable device for supplying the fluid infusion device 100 with power, including, but not limited to, a battery. In one example, the power supply 110 can be removable relative to the housing 106, however, the power supply 110 can be fixed within the housing 106. The controller 112 is in communication with the user interface 102, display 104, power supply 110 and drive system 114. The controller 112 controls the operation of the fluid infusion device 100 based on patient specific operating parameters. For example, the controller 112 controls the supply of power from the power supply 110 to the drive system 114 to activate the drive system 114 to dispense fluid from the fluid reservoir system 116. Further detail regarding the control of the fluid infusion device 100 can be found in U.S. Pat. Nos. 6,485,465 and 7,621,893, the relevant content of which was previously incorporated herein by reference.

The drive system 114 cooperates with the fluid reservoir system 116 to dispense the fluid from the fluid reservoir system 116. In one example, the drive system 114 includes a motor 118, a gear box 120, a drive screw 122 and a slide 124. The motor 118 receives power from the power supply 110. In one example, the motor 118 is an electric motor. The motor 118 includes an output shaft 126, which is coupled to the gear box 120. In one embodiment, the gear box 120 is a reduction gear box. The gear box 120 includes an output shaft 128, which is coupled to the drive screw 122.

The drive screw 122 includes a generally cylindrical distal portion 130 and a generally cylindrical proximal portion 132. The distal portion 130 has a diameter, which can be larger than a diameter of the proximal portion 132. The distal portion 130 includes a plurality of threads 134. The threads 134 are generally formed about an exterior circumference of the distal portion 130. The proximal portion 132 is generally unthreaded, and can be sized to be received within a portion of the slide 124. Thus, the proximal portion 132 can serve to align the drive screw 122 within the slide 124 during assembly, for example.

The slide 124 is substantially cylindrical and includes a distal slide end 136, a proximal slide end 138 and a plurality of threads 140. The distal slide end 136 is adjacent to the motor 118 when the slide 124 is in a first, fully retracted position and the proximal slide end 138 is adjacent to the drive screw 122 when the slide 124 is in the first, fully retracted position. The proximal slide end 138 includes a projection 142, which cooperates with the fluid reservoir system 116 to dispense the fluid from the fluid reservoir system 116. In one example, the projection 142 can have a diameter that is smaller than a diameter of a remainder of the slide 124.

The projection 142 of the proximal slide end 138 includes a first coupling device 144. The first coupling device 144 cooperates with the fluid reservoir system 116 to provide a force or resistance against the movement of a portion of the fluid reservoir system 116 relative to the slide 124. In one example, the first coupling device 144 includes, but is not limited to, a magnet, such as a permanent magnet or an electromagnet. Generally, any suitable magnetic material may be employed, including, but not limited to, a permanent magnet material or a higher magnetic density material. The slide 124 can be overmolded about the first coupling device 144 to couple the first coupling device 144 to the projection 142, or the first coupling device 144 can be coupled to the projection 142 through a suitable technique, such as adhesives, ultrasonic welding, mechanical fasteners, etc. It should be noted that the use of the projection 142 is merely exemplary, as the slide 124 need not include a projection 142 such that the proximal slide end 138 can be flat or planar, and in this example, the first coupling device 144 can be positioned adjacent to the flat or planar proximal slide end 138.

Figure 4:
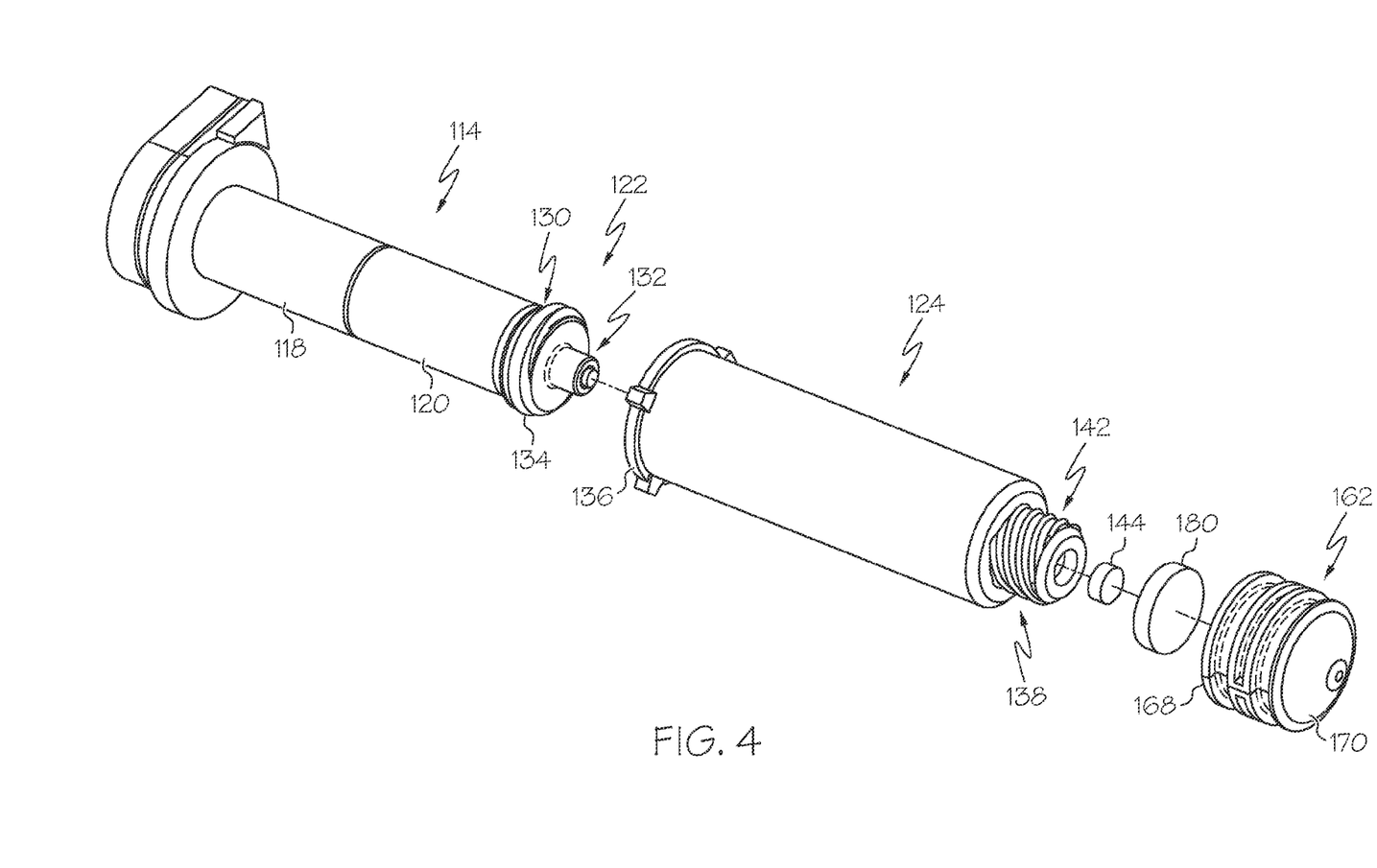
FIG. 4 is a partially exploded perspective view of the drive system and a portion of the fluid reservoir system of the fluid infusion device of FIG. 1.

In one example, the first coupling device 144 is coupled to the projection 142 so as to be positioned substantially circumferentially about the projection 142, however, the first coupling device 144 can be coupled to the projection 142 so as to be disposed partially circumferentially about the projection 142. Thus, the first coupling device 144 does not need to be positioned substantially symmetrically about a longitudinal axis L of the slide 124, rather, the first coupling device 144 can be positioned asymmetrically about the longitudinal axis L. In one example, the first coupling device 144 is an annular disk (FIG. 4), however, the first coupling device 144 can have any desired shape. In addition, it should be noted that the size of the first coupling device 144 is merely exemplary, as the first coupling device 144 can have any size and shape suitable to provide a force or resistance against the movement of a portion of the fluid reservoir system 116.

The plurality of threads 140 of the slide 124 are formed along an interior surface 124a of the slide 124 between the distal slide end 136 and the proximal slide end 138. Generally, the threads 140 do not extend into the projection 142 of the proximal slide end 138. The threads 140 are formed so as to threadably engage the threads 134 of the drive screw 122. Thus, the rotation of the drive screw 122 causes the linear translation of the slide 124.

In this regard, the slide 124 is generally sized such that in a first, retracted position, the motor 118, the gear box 120 and the drive screw 122 are substantially surrounded by the slide 124. The slide 124 is movable to a second, fully extended position (FIG. 3) through the operation of the motor 118. The slide 124 is also movable to a plurality of positions between the first, retracted position and the second, fully extended position via the operation of the motor 118. Generally, the operation of the motor 118 rotates the output shaft 126, which is coupled to the gear box 120. The gear box 120 reduces the torque output by the motor 118, and the output shaft 128 of the gear box 120 rotates the drive screw 122, which moves along the threads 140 formed within the slide 124. The movement or rotation of the drive screw 122 relative to the slide 124 causes the movement or linear translation of the slide 124 within the housing 106. The advancement of the slide 124 into a portion of the fluid reservoir system 116 causes the fluid reservoir system 116 to dispense fluid.

With reference to FIG. 2, the fluid reservoir system 116 is shown. The fluid reservoir system 116 includes a reservoir cap or connector body 150 and a fluid reservoir 152. The connector body 150 creates a fluid path from the fluid reservoir 152 to the body of the patient. In one exemplary embodiment, the connector body 150 is removably coupled to the housing 106, through any suitable technique, such as threads, press-fitting, etc. Generally, the connector body 150 is suitably sized and configured to accommodate the replacement of fluid reservoirs 152 (which are typically disposable) as needed. In one example, the connector body 150 accommodates the fluid path from the fluid reservoir 152 to a tube 156. The tube 156 represents the fluid flow path that couples the fluid reservoir 152 to an infusion unit that couples the tube 156 to the patient (not shown). In one example, the tube 156 is coupled to the fluid reservoir 152 via a connector needle 158, which is coupled to the connector body 150 and pierces a septum 159 associated with the fluid reservoir 152. It should be noted, however, that any suitable technique could be employed to create a fluid path from the fluid reservoir 152 to the patient, and thus, this embodiment is merely exemplary.

The fluid reservoir 152 includes a body or barrel 160 and a stopper 162. The barrel 160 has a first or distal barrel end 164 and a second or proximal barrel end 166. Fluid F is retained within the barrel 160 between the distal barrel end 164 and the proximal barrel end 166. The distal barrel end 164 is positioned adjacent to the slide 124 when the fluid reservoir 152 is assembled in the housing 106. Generally, the distal barrel end 164 can have an open perimeter or be circumferentially open such that the slide 124 is receivable within the barrel 160 through the distal barrel end 164. The proximal barrel end 166 defines a port 166a, which receives the connector needle 158 to define the fluid path. The proximal barrel end 166 can have any desirable size and shape configured to mate with at least a portion of the connector body 150.

Figure 3:
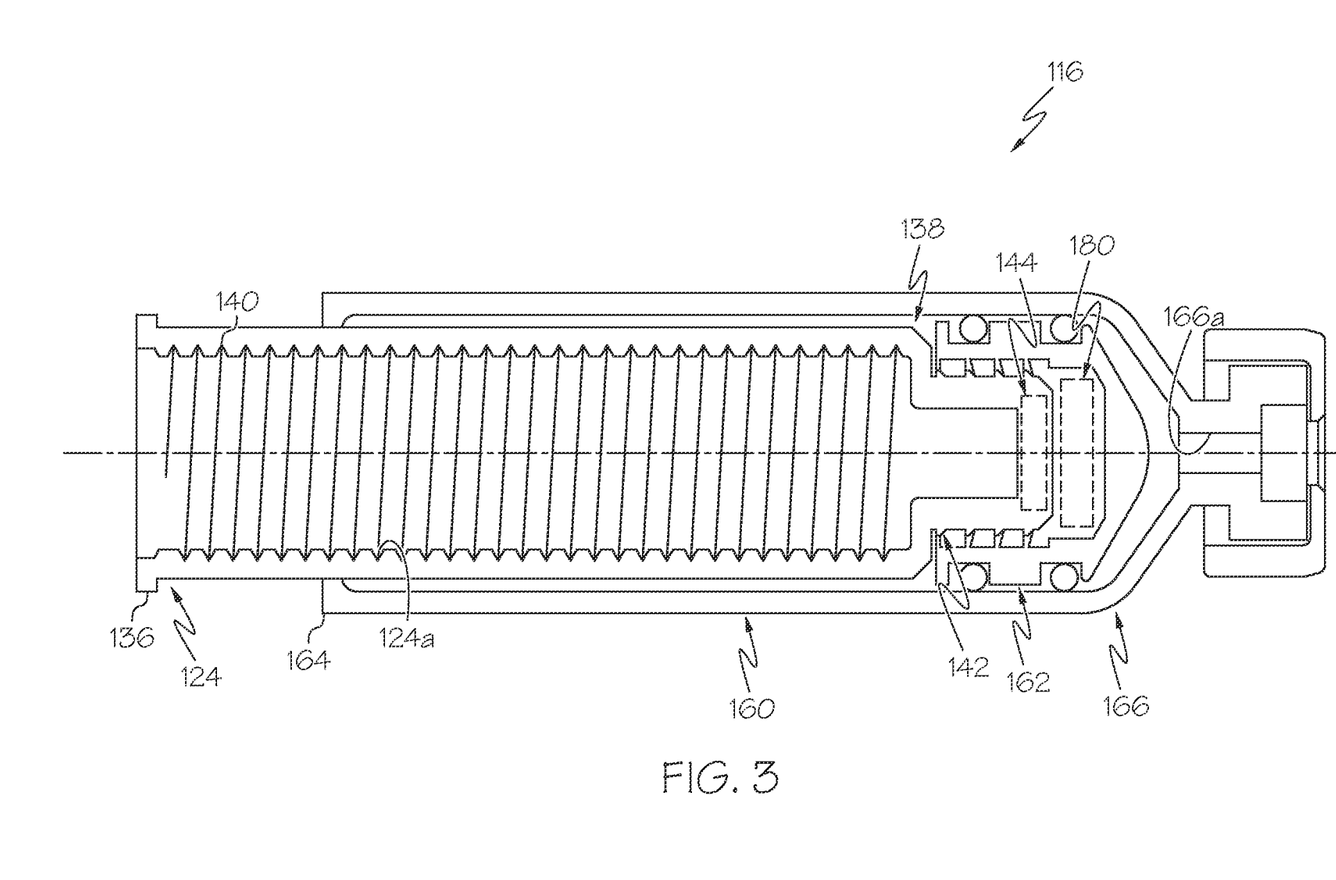
FIG. 3 is a detail cross-sectional view of a portion of a drive system and a portion of the fluid reservoir system of the fluid infusion device of FIG. 1.

The stopper 162 is disposed within the barrel 160. The stopper 162 is movable within and relative to the barrel 160 to dispense fluid from the fluid reservoir 152. When the barrel 160 is full of fluid, the stopper 162 is adjacent to the distal barrel end 164, and the stopper 162 is movable to a position adjacent to the proximal barrel end 166 to empty the fluid from the fluid reservoir 152 (FIG. 3). In one example, the stopper 162 is substantially cylindrical, and includes a distal stopper end 168, a proximal stopper end 170, at least one friction element 172 and a counterbore 174 defined from the distal stopper end 168 to the proximal stopper end 170.

The distal stopper end 168 is open about a perimeter of the distal stopper end 168, and thus, is generally circumferentially open. The proximal stopper end 170 is closed about a perimeter of the proximal stopper end 170 and is generally circumferentially closed. The proximal stopper end 170 includes a slightly conical external surface, however, the proximal stopper end 170 can be flat, convex, etc. The at least one friction element 172 is coupled to the stopper 162 about an exterior surface 162a of the stopper 162. In one example, the at least one friction element 172 comprises two friction elements, which include, but are not limited to, O-rings. The friction elements 172 are coupled to circumferential grooves 176 defined in the exterior surface 162a of the stopper 162. Generally, the circumferential grooves 176 are defined in the exterior surface 162a between the distal stopper end 168 and the proximal stopper end 170, and may be substantially equally spaced from each other. The friction elements 172 may have a limited ability to prevent the stopper 162 from moving freely within the barrel 160. Further, in certain instances, it may be desirable to have a minimal friction between the friction elements 172 and the barrel 160.

The counterbore 174 receives the projection 142 of the slide 124 such that the movement of the slide 124 causes the movement of the stopper 162. In one example, the counterbore 174 includes threads 178, however, the projection 142 of the slide 124 is not threadably engaged with the stopper 162. Thus, the threads 178 illustrated herein are merely exemplary. The counterbore 174 includes a second coupling device 180 adjacent to the proximal stopper end 170. The second coupling device 180 mates with the first coupling device 144 to further resist or prevent the inadvertent movement of the stopper 162. Thus, the first coupling device 144 and the second coupling device 180 provide a safety coupling that further prevents the inadvertent movement of the stopper 162, thereby further reducing the likelihood of unwanted dispersion of fluid from the fluid reservoir 152. In one example, the first coupling device 144 and the second coupling device 180 has an attractive force that ranges from less than about 0.30 lbs of force for a 42 inch long infusion set. Generally, the attractive force required will vary with the size of the reservoir 152 and the pressure acting on the infusion set.

Figure 5:
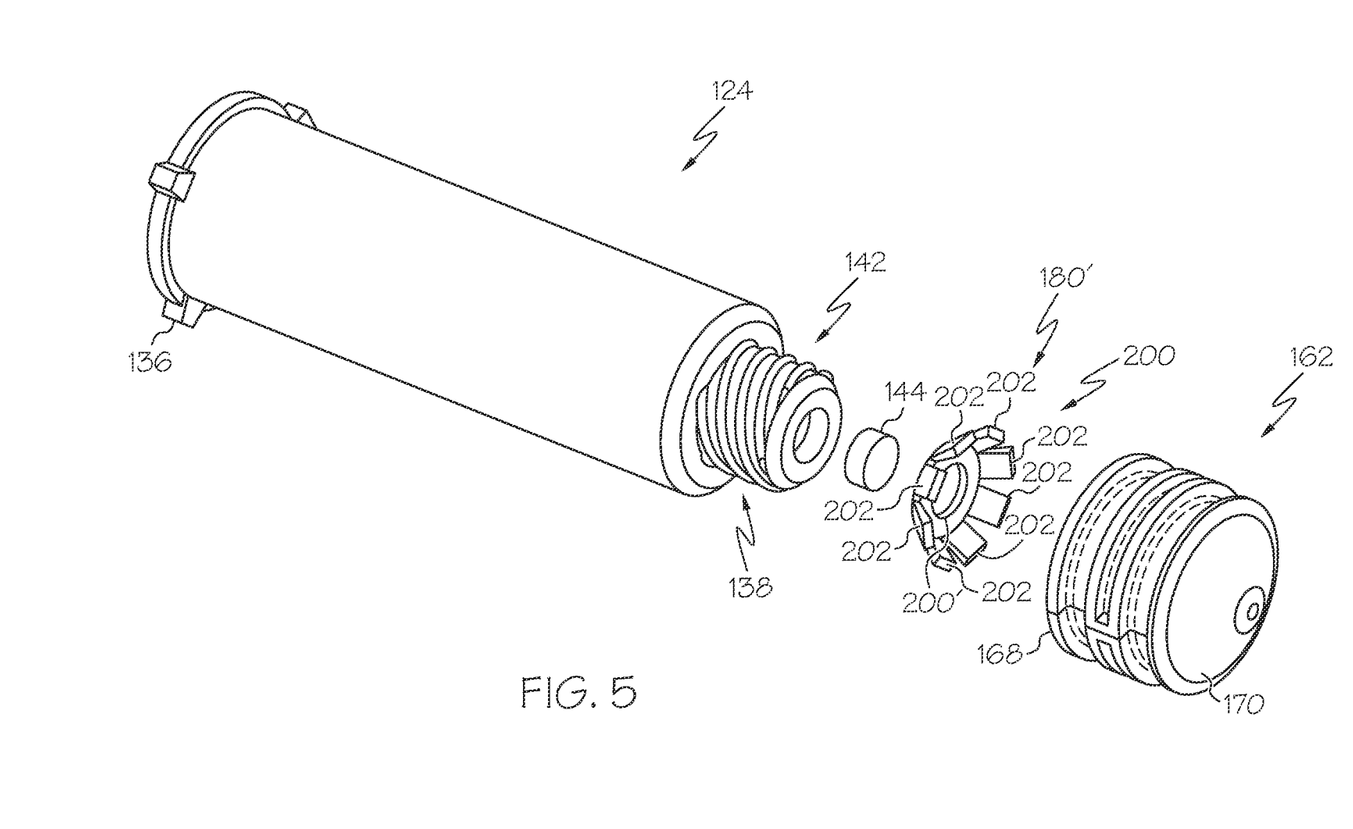
FIG. 5 is a perspective view of a portion of the drive system and a portion of the fluid reservoir system including a second coupling device according to one of various embodiments.

In one example, the second coupling device 180 includes, but is not limited to, a ferromagnetic material, which is attractive to the permanent magnet of the first coupling device 144. Generally, the second coupling device 180 can be composed of any suitable material attractive to the first coupling device 144. In one example, the second coupling device 180 can be composed of a magnetically attractive material with corrosion resistance. It should be noted that the first coupling device 144 can include a ferromagnetic material, and the second coupling device 180 can include the permanent magnet, if desired. Further, the use of a permanent magnet is merely exemplary, as the first coupling device 144 or the second coupling device 180 can include an electromagnet, if desired. The second coupling device 180 is disposed substantially circumferentially about the counterbore 174 near the proximal stopper end 170, however, the second coupling device 180 could be disposed adjacent to the distal stopper end 168, and further, the second coupling device 180 need not be disposed circumferentially about the proximal stopper end 170. Thus, the location and size of the second coupling device 180 is merely exemplary. Further, while the second coupling device 180 is illustrated as being substantially symmetrical with respect to a longitudinal axis L2 of the fluid reservoir 152, the second coupling device 180 can be asymmetrical with respect to the longitudinal axis L2. The second coupling device 180 can be formed with the stopper 162, or can be coupled to the stopper 162 through a suitable manufacturing technique, such as ultrasonic welding, adhesives, mechanical fasteners, etc. In one example, the second coupling device 180 can be a ferromagnetic disk (FIG. 4), which can be molded into the stopper 162 (FIG. 3). In another example, with brief reference to FIG. 5, a second coupling device 180' comprises a disc 200, defining a central opening 200' and having at least one or a plurality of outwardly extending flanges 202. The flanges 202 are spaced about a perimeter of the disc 200, and extend in a direction towards the flow of fluid through the fluid reservoir system 116. The use of the flanges 202 assists in the coupling and retention of the second coupling device 180' within the stopper 162.

With reference back to FIG. 2, with the housing 106 assembled with the power supply 110, the controller 112 and the drive system 114, the fluid reservoir system 116 can be coupled to the housing 106. In one example, a full fluid reservoir 152 is inserted into the housing 106 such that the stopper 162 is adjacent to the projection 142 of the slide 124 and the first coupling device 144 is attracted to the second coupling device 180. The magnetic attraction or attractive force between the first coupling device 144 and the second coupling device 180 prevents the movement of the stopper 162 within the barrel 160 in instances of low fluid pressure and low contact friction between the friction elements 172 and a wall of the barrel 160. The advancement of the drive screw 122 causes the slide 124 to translate linearly.

When the motor 118 ceases operation or is stationary, the slide 124 and the stopper 162 stop moving, and the stopper 162 remains positioned in the barrel 160 due to the friction between the friction elements 172 and a wall of the barrel 160, and the attractive force between the first coupling device 144 and the second coupling device 180 (FIG. 3). Thus, the first coupling device 144 and the second coupling device 180 cooperate to resist or prevent unintentional movement of the stopper 162 away from the slide 124. In the event that the patient requests a rewind of the slide 124 (e.g. movement of the slide 124 in a reverse direction or direction opposite of fluid flow), the torque of the motor 118 overcomes the magnetic attraction or attractive force between the first coupling device 144 and the second coupling device 180 to allow the slide 124 to move or retract without substantially moving the stopper 162.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A safety coupling for a fluid infusion device, comprising:
a first coupling device coupled to a slide of a drive system of the fluid infusion device, the slide including a proximal end opposite a distal end, the proximal end including a projection and the first coupling device is coupled to the projection; and
a second coupling device coupled to a stopper of a fluid reservoir associated with the fluid infusion device, the stopper including a distal stopper end opposite a proximal stopper end with a counterbore defined through the distal stopper end, the second coupling device coupled to the proximal stopper end, the fluid reservoir removably received in a housing of the fluid infusion device and including a barrel, with the stopper disposed in the barrel and the slide receivable within the barrel such that the proximal end of the slide is adjacent to the distal stopper end and the projection is received within the counterbore of the stopper to mate the first coupling device with the second coupling device,
wherein the first coupling device is a magnet, the second coupling device is a ferromagnetic material and the first coupling device and the second coupling device cooperate to resist the movement of the stopper away from the slide.

2. The coupling of claim 1, wherein the first coupling device and the second coupling device provide an attractive force that resists the further movement of the stopper away from the drive system.

3. The coupling of claim 1, wherein the first coupling device is coupled to the slide so as to be positioned substantially symmetrically about a longitudinal axis of the slide.

4. The coupling of claim 1, wherein the second coupling device is coupled to the stopper so as to be positioned substantially symmetrically about a longitudinal axis of the fluid reservoir.

5. The coupling of claim 1, wherein the second coupling device is a disc having a plurality of outwardly extending flanges spaced about a perimeter of the disc, each of the plurality of outwardly extending flanges coupled at the perimeter of the disc at an angle.

6. A safety coupling for a fluid infusion device, comprising:
a first coupling device coupled to a slide of a drive system of the fluid infusion device, the slide including a proximal end opposite a distal end, the proximal end including a projection and the first coupling device is coupled to the projection; and
a second coupling device coupled to a stopper of a fluid reservoir associated with the fluid infusion device, the stopper including a distal stopper end opposite a proximal stopper end with a counterbore defined through the distal stopper end, the second coupling device coupled to the proximal stopper end, the fluid reservoir removably received in a housing of the fluid infusion device and including a barrel, with the stopper disposed in the barrel and the slide receivable within the barrel such that the proximal end of the slide is adjacent to the distal stopper end and the projection is received within the counterbore of the stopper to mate the first coupling device with the second coupling device,
wherein the first coupling device is a magnet, the second coupling device is a disc having a plurality of outwardly extending flanges spaced about a perimeter of the disc, with each of the plurality of outwardly extending flanges coupled at the perimeter of the disc at an angle, and the first coupling device and the second coupling device cooperate to resist the movement of the stopper away from the slide.

* * * * *